US010449227B2

(12) United States Patent
McLaughlin et al.

(10) Patent No.: US 10,449,227 B2
(45) Date of Patent: Oct. 22, 2019

(54) CONJUGATES FOR IMMUNOTHERAPY

(71) Applicants: H. LEE MOFFITT CANCER CENTER AND RESEARCH INSTITUTE, INC., Tampa, FL (US); UNIVERSITY OF SOUTH FLORIDA, Tampa, FL (US)

(72) Inventors: Mark McLaughlin, Tampa, FL (US); David L. Morse, Tampa, FL (US); Shari Pilon-Thomas, Tampa, FL (US); Scott Antonia, Land O'Lakes, FL (US)

(73) Assignees: H. Lee Moffitt Cancer Center and Research Institute, Inc., Tampa, FL (US); University of South Florida, Tampa, FL (US)

( * ) Notice: Subject to any disclaimer, the term of this patent is extended or adjusted under 35 U.S.C. 154(b) by 35 days.

(21) Appl. No.: 15/321,316

(22) PCT Filed: Jun. 26, 2015

(86) PCT No.: PCT/US2015/038057
§ 371 (c)(1),
(2) Date: Dec. 22, 2016

(87) PCT Pub. No.: WO2015/200828
PCT Pub. Date: Dec. 30, 2015

(65) Prior Publication Data
US 2017/0202902 A1    Jul. 20, 2017

Related U.S. Application Data

(60) Provisional application No. 62/018,372, filed on Jun. 27, 2014.

(51) Int. Cl.
| | |
|---|---|
| *A61K 38/08* | (2019.01) |
| *A61K 49/00* | (2006.01) |
| *A61K 38/19* | (2006.01) |
| *A61K 38/20* | (2006.01) |
| *A61K 38/17* | (2006.01) |
| *A61K 47/64* | (2017.01) |
| *A61K 38/00* | (2006.01) |
| *A61K 39/00* | (2006.01) |

(52) U.S. Cl.
CPC ............ *A61K 38/08* (2013.01); *A61K 38/179* (2013.01); *A61K 38/195* (2013.01); *A61K 38/208* (2013.01); *A61K 47/64* (2017.08); *A61K 47/646* (2017.08); *A61K 49/0032* (2013.01); *A61K 49/0056* (2013.01); *A61K 38/00* (2013.01); *A61K 2039/60* (2013.01); *C07K 2319/00* (2013.01)

(58) Field of Classification Search
None
See application file for complete search history.

(56) References Cited

FOREIGN PATENT DOCUMENTS

WO    WO2010/027827    * 3/2010    ............ C07K 14/47

OTHER PUBLICATIONS

Cheever et al, Clinical Cancer Research, 2009, vol. 15, pp. 5323-5337 (Year: 2009).*
Abstract of Nakamura et al, Acta Endocrinol (Copenh), Oct. 1992, vol. 127, No. 4, pp. 324-330 (Year: 1992).*
Gierten et al, British Journal of Pharmacology, 2008, vol. 154, pp. 1680-1690) (Year: 2008).*
Thunumadathil, Journal of Amino acids, 2012, Article ID 967347, 13 pages (Year: 2012).*
Armer and Smelt (Current Medicinal Chemistry, 2004, vol. 11, pp. 3017-3028) (Year: 2004).*
Abstract of Heitman et al (Med Res Rev. 2008, vol. 28, pp. 975-1011) (Year: 2008).*
Afshar-Oromieh et al, Journal of Nuclear Medicine, 2016, vol. 10, suppl. 3, pp. 79S-89S (Year: 2016).*
Hasenstein et al, Neoplasia, 2012, vol. 14, pp. 131-140 (Year: 2012).*
Boyer, Current Topics in Medicinal Chemistry, 2002, vol. 2, pp. 973-1000) (Year: 2002).*
Dienus et al, Archives of Dermatology Reserach, 2010, pp. 725-731 (Year: 2010).*
Criscitello et al, Expert Opinion on Investigational Drugs, 2014, vol. 23, pp. 599-610 (Year: 2014).*
Azzas et al, Current Medicinal Chemistry, 2010, vol. 17, pp. 1255-1299); (Year: 2010).*
Ollauri-Ibanez et al, Expert Opinion on Biologcal Therapy, 2017, vol. 17, pp. 1053-1063 (Year: 2017).*
Friedrich et al (Molecular Cancer Therapetuics, 2012, vol. 11, pp. 2664-2673). (Year: 2012).*
Kiewe et al (Clinical Cancer Research, 2006, vol. 12, pp. 3085-3091). (Year: 2006).*
Ruf et al (Journal of Translational Medicine, 2012, vol. 10, No. 219, 10 pages) (Year: 2012).*
Lee et al, Cancer Immunol Immunother, 2012, vol. 61, pp. 1805-1817 (Year: 2012).*
Gerstmayer et al, Journal of Immunology, 1997, vol. 158, pp. 4584-4590 (Year: 1997).*
Liu et al, Journal of Immunotherapy, 2010, vol. 33, pp. 500-509 (Year: 2010).*
Abken et al, Trends in Immunology, 2002, vol. 23, pp. 240-245 (Year: 2002).*
Melchers et a, Retrovirology, 2011, vol. 8, pp. 48-62 (Year: 2011).*
Pollok et al, European Journal of Immunology, 1994, vol. 24, pp. 367-374 (Year: 1994).*
Oh et al, Journal of Korean Medical Science, 2011, vol. 26, pp. 1270-1276 (Year: 2011).*
Peng et al, Journal of Immunology, 1999, vol. 163, pp. 250-258 (Year: 1999).*

* cited by examiner

*Primary Examiner* — Karen A. Canella
(74) *Attorney, Agent, or Firm* — Meunier Carlin & Curfman LLC

(57) ABSTRACT

The current invention pertains to a molecular conjugate comprising an antagonist of a cell surface receptor specific to a target cell and an immune effector, such as a T cell modulator, conjugated to the antagonist. The target cell can be a cell responsible for development of a disease in a subject, for example, a cancer cell. In certain embodiments, the immune effector is an immune effector protein or an immune effector fragment thereof. The current invention also pertains to a method of treating a disease in a subject, the method comprising administering to the subject a pharmaceutically effective amount of the molecular conjugates of the current invention to the subject. The methods of the current invention can be used to treat cancer, such as breast cancer, ovarian cancer, prostate cancer, lung cancer, pancreatic cancer, or melanoma.

9 Claims, 3 Drawing Sheets

CONJUGATES FOR IMMUNOTHERAPY

CROSS-REFERENCE TO RELATED APPLICATIONS

The present application is the National Stage of International Application No. PCT/US2015/038057, filed Jun. 26, 2015, which claims the benefit of U.S. Provisional Application Ser. No. 62/018,372, filed Jun. 27, 2014, which is hereby incorporated by reference herein in its entirety, including any figures, tables, nucleic acid sequences, amino acid sequences, or drawings.

BACKGROUND OF THE INVENTION

Avoiding immune destruction is now recognized as one of the ten hallmarks of cancer [32]. Most tumors are immunogenic, but evade immune-mediated destruction by actively blunting the immune response. The FDA-approved checkpoint inhibitors, anti-CTLA4 and anti-PD1, provide overall survival advantages for a majority and durable complete responses for a minority of melanoma patients; the combination of anti-CTLA4 and anti-PD1 gives a slight majority of melanoma patients durable complete responses [33]. These untargeted, systemically administered checkpoint inhibitors are safe and effective immunotherapy agents that counteract tumor immunosuppression mechanisms [3-5]. Unfortunately, these checkpoint inhibitors alone cause dose-limiting adverse immune-related events and the combination of these checkpoint inhibitors leads to greater rates of adverse immune-related events [5]. Recently, anti-PD1 has been FDA approved to treat non-small cell lung cancer (NSCLC) suggesting that, like melanoma, NSCLC may develop disease-specific T cells that are immune suppressed, making NSCLC tumors susceptible to immunotherapy.

BRIEF SUMMARY OF THE INVENTION

Immunotherapy can be effective in most solid tumors where it has been investigated using systemic delivery of checkpoint inhibitors to enhance the immune response. While effective systemic doses of the checkpoint inhibitors have been found, the immune-related adverse events seen in patients can be severe and life threatening. This can be due to activation of immune effector cells outside of the tumor, which leads to inflammatory damage of normal tissues. Therefore, modulating and/or controlling immune signals directed to target cells may be beneficial. If adverse immune-related events could be reduced and more effective immunotherapy doses could be concentrated at the tumor microenvironment, a greater percentage of patients would have durable complete responses.

Recent approaches pursued to tailor desirable immune responses include the use of bispecific antibodies and chimeric antigen receptor (CAR) T cells. Described herein is a simpler approach, in which a known antagonist targeting ligand can be used to direct immune effectors to the targeted cells. There are many possible targeting ligands known; one of the best known is luteinizing hormone-releasing hormone (LHRH). LHRH ligand has been used to deliver a lytic peptide cytotoxic agent to target cells. This approach has been shown to effectively limit systemic toxicity by using the limited expression of the LHRH receptor as a way of delivering the cytotoxic agents specifically to the tumor microenvironment while sparing normal vital organ tissue.

The current invention provides a molecular conjugate comprising:

a) an antagonist of a cell surface receptor specific to a target cell; and b) an immune effector conjugated to the antagonist.

The target cell can be a cell responsible for development of a disease in a subject. In certain embodiments, the target cell is a cancer cell and the cell surface receptor can be specific to the cancer cell.

The antagonist of the cell surface receptor can be a peptide, peptoid or aptamer.

In certain embodiments, the immune effector is an immune effector protein or an immune effector fragment thereof.

The current invention also provides methods of treating a disease in a subject. The methods comprise administering to the subject a pharmaceutically effective amount of a molecular conjugate comprising:

a) an antagonist of a cell surface receptor specific to a target cell wherein the target cell is responsible for development of the disease in the subject; and b) an immune effector conjugated to the antagonist.

The methods of the current invention can be designed to treat any disease where the disease causing cells express specific molecules, particularly, on the cell surface. For example, a cancer cell expresses specific receptors on its surface. Accordingly, the current invention provides a method of treating cancer by administering to the subject a pharmaceutically effective amount of a molecular conjugate comprising a) an antagonist of a cell surface receptor specific to a cancer cell; and b) an immune effector conjugated to the antagonist.

The invention also provides a method for delivering a molecular conjugate to a cell, the method comprising administering to the cell in vitro or in vivo a molecular conjugate of the invention. In some embodiments, the cell is a diseased cell, such as a cancer cell.

BRIEF DESCRIPTION OF THE DRAWINGS

FIG. 2A is a synthesis scheme for Dmt-Tic-Vivo-Tag-680-TTM. FIG. 2B shows a representation of an antibody-drug conjugate.

FIG. 3A shows a representation of an immunosuppressed tumor microenvironment in which signal 2 T cell interactions are inhibited. FIGS. 3B-3F show some of the targeted Dmt-Tic-TTMs that can be prepared.

DETAILED DESCRIPTION OF THE INVENTION

Figure 1:
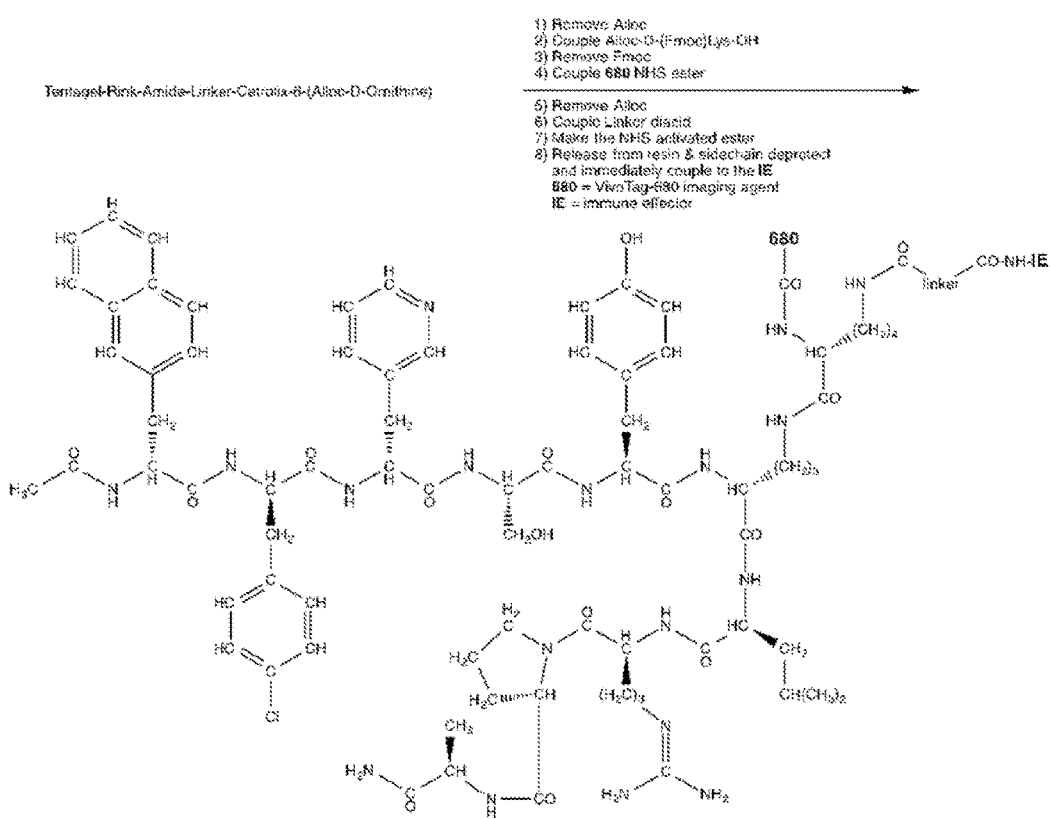
FIG. 1 shows a synthesis scheme for LHRH antagonist conjugates with a fluorescent imaging agent and immune effectors.

If adverse immune-related events could be reduced and more effective immunotherapy doses could be concentrated at the tumor microenvironment, a greater percentage of patients would have durable complete responses.

The current invention provides a molecular conjugate comprising:

a) an antagonist of a cell surface receptor specific to a target cell (also referred to herein as a "targeting ligand"); and b) an immune effector conjugated to the antagonist.

By conjugating immune effectors with a targeting ligand, the molecular conjugate can specifically concentrate at a target anatomical site (i.e., at a site having cells that are targets for the targeting ligand). The target cell can be a cell responsible for development of a disease in a subject. In certain embodiments, the target cell is a cancer cell and the cell surface receptor can be specific to the cancer cell. In some embodiments, the immune effector is a T cell modulator, and the resulting molecular conjugate is referred to herein as a "targeted T cell modulator" or "TTM". By conjugating T cell modulator ligands with a targeting ligand, the TTM can specifically concentrate at the tumor and promote a stronger immune response in the targeted tumor relative to untargeted TTMs at the same dose.

In the case of cancer applications, for example, the targeted cell surface receptor that is the target of the antagonist (the targeting ligand) is mainly expressed on the cancerous cells, but not the normal non-cancerous cells, this ensures delivery of the conjugated immune effector directly tumor, thus sparing normal tissues. Antagonistic anti-cancerous action of the targeting ligand combined with the immune-mediated killing can provide a powerful therapeutic effect on the tumor while keeping systemic toxicity to a minimum.

This strategy is flexible in that one or more copies of the targeting ligand, or even more than one type of targeting ligand, can be conjugated with the immune effector. Again, in the case of cancer, the conjugate is designed to reduce out-of-tumor immune activation and provide a greater therapeutic window with which to safely activate the immune system in the tumor microenvironment.

The antagonist of the cell surface receptor can be a peptide, peptoid or aptamer, for example.

In certain embodiments, the immune effector is an immune effector protein or an immune effector fragment thereof.

The current invention provides molecular conjugates and uses thereof to enhance the safety and efficacy of immunotherapy by specifically delivering immune effectors to target cells via a receptor antagonist specific for receptors present on the target cell. Thus, simple to produce and high affinity antagonists for receptors found exclusively or almost exclusively on the target cells can be used to deliver immune effectors to the target cell microenvironment.

Merging immune co-stimulatory signals with the ability of a receptor antagonist to target specific cells has the potential to dramatically improve the risk/benefit ratio of disease treatments. This is especially critical when multiple immune modulators are combined and the risk of uncontrolled autoimmunity is increased. The current invention provides merging of these two powerful approaches as a way of profoundly stimulating an immune response with greater specificity in target cells.

Immune cells use a complex array of signals to communicate to each other when confronting its targets, for example, pathogens or cancer cells. These signals include both secreted chemokines and receptor-ligand interactions, which alter the level of immune activation in various effector cells. The goal of this system is to have an appropriate activated immune response towards foreign antigens, prevent autoimmunity, generate long-term immunity, and allow for an orderly deactivation once the threat is eliminated. The interface between an effector T cell and antigen presenting cells is called the immune synapse. Within the synapse, the first activation signal for a T cell is binding of the T cell receptor to a major histocompatibility complex (MHC) loaded with a target antigen. This is not sufficient for activation, and full activation requires secondary co-stimulatory signals such as CD86, 4-1BBL, and OX40L binding to their respective receptors on the T cell (CD28, 41BB, OX40). When multiple costimulatory signals are used simultaneously, this results in even greater effector cell activation. Tagging tumor cells with specific cell surface receptor antagonist bound versions of these signals can result in enhanced activation and survival of T cells among the tumor infiltrating lymphocytes and eradication of tumor cells, for example, via perforin/granzyme cytolytic killing.

The current invention provides a receptor antagonist conjugated to immune effectors, for example, co-stimulators. The system is easily produced, and unbound construct is cleared from the body more quickly compared to a larger antibody. This approach is very translatable, and has the potential to revolutionize immunotherapy, for example, cancer therapy and outcomes by eradicating refractory disease.

Existing tumors and metastases that avoid normal immune response destruction have done so by taking advantage of many different immune suppressive strategies. Targeting of immune effectors to the tumor microenvironment can overcome these immune suppressive strategies. Combinations of immunomodulators may be required to maximize responses to immunotherapy. Since these targeted constructs can preferentially build up in the tumor over time and provide co-stimulation to tumor responsive T cells nearby, this is likely to result in less autoimmunity. Targeted agents such as these constructs would be ideally suited to combine with other immunomodulators, for example, indoleamine 2,3 dioxygenase inhibitors, to deliver a more potent immune stimulation without excessive collateral damage.

Accordingly, the current invention provides a molecular conjugate comprising a receptor antagonist conjugated to an immune effector. The molecular conjugate, when bound to the target cell can initiate or enhance an immune response to the target cell expressing the receptor which can lead to immune system mediated destruction of the target cell. Accordingly, the molecular conjugate of the current invention can be used to specifically destroy cells responsible for development of a disease. A person of ordinary skill in the art can determine which diseases are caused by specific cells and design molecular conjugates targeted to the specific cells. As such, the current invention provides a method of treating a disease by administering the molecular conjugates of the current invention to a subject in need of such treatment.

Optionally, the molecular conjugate includes one or more detectable moieties attached thereto (e.g., an imaging agent such as a fluorescent label or tag) to image the conjugate in vitro or in vivo. The detectable moiety may be coupled directly or indirectly to the antagonist, the immune effector molecule, or both. Depending upon the imaging modality or modalities, an instrument may be necessary to visualize the imaging agent of the conjugate.

For the purpose of the current invention, an antagonist is a molecule that binds with affinity to a receptor on the surface of the target cell and inhibits receptor response. Antagonists are typically not internalized upon binding to the target cell. An antagonist may be a partial antagonist or a pure (full) antagonist (e.g., a silent antagonist), and may be competitive, non-competitive, or uncompetitive. In some embodiments, the antagonist is an irreversible antagonist that binds to the receptor target and is generally not removed.

For the purpose of the current invention, an immune effector is a molecule capable of initiating or enhancing an immune response, such as a T-cell mediated response, which leads to the immune system mediated destruction of the target cell. Immune effectors that initiate or enhance a T-cell mediated response are referred to herein as a "T cell modulator". In embodiments in which the immune effector is a T cell modulator, the resulting molecular conjugate is referred to herein as a "targeted T cell modulator" or "TTM".

A TTM can initiate or enhance an immune response by activating T-cells or inhibiting other signals and/or molecules that inhibit T-cells, for example, agents that cause T-cell anergy. TTMs can also act by stimulating T-cell proliferation, e.g., a T-cell growth factor. Particularly, the immune effector can initiate or enhance cellular immunity directed to the target cell.

In certain embodiments, the immune effector molecule is a protein or an immune effector fragment of the protein. In some embodiments, the conjugate includes a single immune effector. In other embodiments, the conjugate includes a plurality of immune effectors of the same type or different types. Non-limiting examples of immune effector proteins include CD86, CD80, 41BBL, OX40, IL-15, Anti-Programmed Death-1 (PD1), anti-B7-H1, IL-12, Anti-CD40, CD40 ligand, IL-7, Anti-CD137 (anti-4-1BB), Anti-TGF-beta, Anti-IL-10 Receptor or Anti-IL-10, FMS-like Tyrosine Kinase 3 Ligand (Flt3L), Anti-Glucocorticoid-Induced TNF Receptor (GITR), chemokine (C-C motif) ligand 21 (CCL21), Anti-OX40, Anti-B7-H4, Anti-Lymphocyte Activation Gene-3 (LAG-3), CD258 (also referred to as LIGHT or TNFSF14), Anti-CTLA4, or an immune effector fragment of any of the foregoing. Additional examples of immune effector molecules are well known to a person of ordinary skill in the art and such embodiments are within the purview of this invention. For example, certain immune effectors are discussed in NCI Immunotherapy Agent Workshop Proceedings and published as Immunotherapy Agent Workshop, Jul. 12, 2007, U.S. Department of Health and Human Services, National Institutes of Health, which is incorporated herein by reference in its entirety. A person of ordinary skill in the art can design the molecular conjugates based on this and similar scientific publications available in the art.

In some embodiments, the antagonist (targeting ligand) of the conjugate is a luteinizing hormone releasing hormone (LHRH) antagonist (e.g., Cetrorelix), or a delta opioid receptor (DOR) ligand antagonist. Examples of DOR antagonists that may be used include, but are not limited to, Dmt-Tic (e.g., DMT-Tic-OH or DMT-Tic-Ala-OH), naltrindole, naltriben, trazodone, buprenorphine, ICI 174,864 (N,N-diallyl-Tyr-Aib-Aib-Phe-Leu), N-Benzylnaltrindole, BNTX (7-Benzylidenenaltrexone), SoRI-9409, ICI 154,129 (N, N-Diallyl-Tyr-Gly-φ-(CH$_2$S)-Phe-Leu-OH, or SDM25N (4bS,8R,8aS,14bR)-5,6,7,8,14,14b-Hexahydro-7-(2-methyl-2-propenyl)-4,8-methanobenzofuro[2,3-a]pyrido[4,3-b]carbazole-1,8a(9H)-diol. Other delta opioid receptor antagonists are described in U.S. Pat. No. 5,352,680 (Portoghese and Takemori), Portoghese P S et al., *J. Med. Chem.*, 1990, 33, 1714-1720, Mosberg H I et al., *Letters in Peptide Science*, 1994, (1(2):69-72, and Korlipara V L et al., *J. Med. Chem.*, 1994, 37, 1881-1885, which are each incorporated herein by reference in its entirety.

In some embodiments, the immune effector of the conjugate is a T-cell modulator, such as anti-PD1, anti-PDL1, CD137, OX40, or CD28.

In some embodiments, the antagonist of the conjugate is the luteinizing hormone releasing hormone (LHRH) antagonist (Cetrorelix), or a delta opioid receptor (DOR) ligand antagonist, and the immune effector of the conjugate is anti-PD1, anti-PDL1, CD137, OX40, CD28, or another T-cell modulator. As indicated above, optionally, a detectable moiety can be added to monitor the conjugate's behavior in vivo or in vitro.

A person of ordinary skill in the art can determine which fragment of an immune effector molecule retains the immune effector function and therefore, one can determine which fragment of the immune effector molecule can be conjugated to the cell surface specific receptor antagonist.

The receptor can be specific to certain target cells, i.e., the receptor is present only on the surfaces of the target cells and is absent from the surfaces of non-target cells or is present on the surfaces of the target cells at a high level and is present on the surfaces of non-target cells at a lower level or a significantly lower level than that of the target cells. For example, the receptor can be specific to a cancer cell, i.e., a receptor which is present only on the surfaces of cancer cells and is absent from the surfaces of normal cells or is present on the surfaces of cancer cells at high level and is present on the surfaces of normal cells at a low level or a significantly lower level. The receptor can also be specific to an infectious agent, i.e., a receptor which is present only on the surfaces of infectious agents and is absent from the surfaces of the host cells or is present on the surfaces of infectious agents at high level and is present on the surfaces of the host cells at a significantly lower level.

The cell surface receptor specific to a cancer cell can be luteinizing hormone release hormone (LHRH) receptor, delta opioid receptor (DOR), melanocortin 1 receptor (MCR1), cell surface associated mucin 1 (MUC1), latent membrane protein 2 (LMP2), epidermal growth factor receptor variant III (EGFRvIII), human epidermal growth factor receptor 2 (HER-2/neu), prostate specific membrane antigen (PSMA), ganglioside antigen 2 (GD2), melanoma antigen recognized by T-cells 1 (MelanA/MART1), Ras mutant, glycoprotein 100, Proteinase3 (PR1), bcr-abl, tyrosinase, Androgen receptor, RhoC, transient receptor potential channel 2(TRP-2), prostate stem cell antigen (PSCA), leukocyte specific protein tyrosine kinase (LCK), high molecular weight melanoma-associated antigen (HMW-MAA), A-kinase anchor protein 4 (AKAP-4), Angiopoietin-1 receptor (Tie 2), vascular endothelial growth factor receptor 2 (VEGFR2), fibroblast activation protein (FAP), platelet derived growth factor receptor b (PDGFR-b), parathyroid hormone related protein, luteinizing hormone related protein, alpha(V)Beta(3)Integrin, six transmembrane antigen of the prostate (STEAP), mesothelin, endoglin, KCNK9, or guanylyl cyclase C (GC-C). Additional examples of receptors specific to cancer cells are well known to a person of ordinary skill in the art and such embodiments are within the purview of this invention. For example, Meyer et al. (2011), Cell-specific aptamers as emerging therapeutics, *Journal of Nucleic Acids*, Volume 2011, Article ID 904750, teaches cancer cell specific receptor, the contents of which are herein incorporated by reference in its entirety, particularly, page 5, the section under "Cell specific aptamers for therapy" continuing on to pages 6 to 13. Additional examples are also disclosed in Cheever et al. (2009), The prioritization of cancer antigens: a national cancer institute pilot project for the acceleration of translational research, *Clinical Cancer Research;* 15:5323-5337, the contents of which are also incorporated herein by reference, particularly, antigen list provided in Table 3, some of which are cell surface receptors that can be used according to the current invention.

Non-limiting examples of receptor antagonists include a peptide antagonist or an aptamer antagonist.

Aptamers are polynucleotide or polypeptide molecules that bind to a specific target molecule. Non-limiting examples of aptamers include: DNA aptamers; RNA aptamers; XNA (nucleic acid analogs or artificial nucleic acids) aptamers; and polypeptide aptamers. Examples of XNA include, but are not limited to, polypeptide nucleic acid (PNA), morpholino and locked nucleic acid (LNA), glycol nucleic acid (GNA), and threose nucleic acid (TNA).

The receptor antagonist can be conjugated to the immune effector in a covalent or a non-covalent manner. The receptor antagonists can be covalently conjugated to the immune effectors directly as contiguous units or indirectly via other moieties such as a molecular linker. Various molecular linkers are known to a person of ordinary skill in the art and certain non-limiting examples are described in "Easy molecular bonding crosslinking technology" published by Thermo Scientific (2012), the contents of which are herein incorporated by reference in its entirety.

In another embodiment of the invention, the receptor antagonist is conjugated to the immune effector in a non-covalent manner. Non-limiting examples of non-covalent binding between the receptor antagonist and the immune effector include electrostatic binding, π-binding, van der Waals interactions, and hydrophobic binding.

The receptor antagonist conjugated to immune effector can be used to specifically deliver the immune effector to target cells, for example, cancer cells. The receptor antagonist can selectively recognize target cells, for example, cells having the receptor on its surface, and thus deliver the immune effector conjugated to the receptor antagonist to the target cells, for example, cancer cells. The immune effector can then initiate and/or enhance immune response directed to the target cell thereby causing immune system mediated destruction of the target cell.

The molecular conjugates of the current invention can thus kill the target cells, for example, cancer cells, without affecting the non-targeted cells, for example, normal cells. As such, the current invention provides compositions and methods for treating a disease in a subject.

The diseases that can be treated, according to compositions and methods of the invention, include cancer, microbial infections and other diseases where the disease causing cells exhibit presence of a specific cell surface receptor that can be exploited to target the diseased cells. Various cancers that can be treated, according to an embodiment of the invention, are well known to a person of ordinary skill in the art and such cancers are within the purview of the current invention. The microbial infections can be viral, fungal, bacterial, protozoan, or prion mediated infections.

Oncological disorders within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment with the present invention include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Examples of cancers that can be treated according to the present invention are listed in Table 1.

Acute Lymphoblastic Leukemia, Adult
Acute Lymphoblastic Leukemia, Childhood
Acute Myeloid Leukemia, Adult
Acute Myeloid Leukemia, Childhood
Adrenocortical Carcinoma
Adrenocortical Carcinoma, Childhood
AIDS-Related Cancers
AIDS-Related Lymphoma
Anal Cancer
Astrocytoma, Childhood Cerebellar
Astrocytoma, Childhood Cerebral
Basal Cell Carcinoma
Bile Duct Cancer, Extrahepatic
Bladder Cancer
Bladder Cancer, Childhood
Bone Cancer, Osteosarcoma/Malignant Fibrous Histiocytoma
Brain Stem Glioma, Childhood
Brain Tumor, Adult
Brain Tumor, Brain Stem Glioma, Childhood
Brain Tumor, Cerebellar Astrocytoma, Childhood
Brain Tumor, Cerebral Astrocytoma/Malignant Glioma, Childhood
Brain Tumor, Ependymoma, Childhood
Brain Tumor, Medulloblastoma, Childhood
Brain Tumor, Supratentorial Primitive Neuroectodermal Tumors, Childhood
Brain Tumor, Visual Pathway and Hypothalamic Glioma, Childhood
Brain Tumor, Childhood
Breast Cancer
Breast Cancer, Childhood
Breast Cancer, Male
Bronchial Adenomas/Carcinoids, Childhood
Burkitt's Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Squamous Neck Cancer with Occult Primary, Metastatic
Stomach (Gastric) Cancer
Stomach (Gastric) Cancer, Childhood
Supratentorial Primitive Neuroectodermal Tumors, Childhood
T-Cell Lymphoma, Cutaneous, see Mycosis Fungoides and Sézary Syndrome -continued Testicular Cancer
Thymoma, Childhood
Thymoma and Thymic Carcinoma
Thyroid Cancer
Thyroid Cancer, Childhood
Transitional Cell Cancer of the Renal Pelvis and Ureter
Trophoblastic Tumor, Gestational
Unknown Primary Site, Carcinoma of, Adult
Unknown Primary Site, Cancer of, Childhood
Unusual Cancers of Childhood
Ureter and Renal Pelvis, Transitional Cell Cancer
Urethral Cancer
Uterine Cancer, Endometrial
Uterine Sarcoma
Vaginal Cancer
Visual Pathway and Hypothalamic Glioma, Childhood
Vulvar Cancer
Waldenström's Macroglobulinemia
Wilms' Tumor
Hairy Cell Leukemia
Head and Neck Cancer
Hepatocellular (Liver) Cancer, Adult (Primary)
Hepatocellular (Liver) Cancer, Childhood (Primary)
Hodgkin's Lymphoma, Adult
Hodgkin's Lymphoma, Childhood
Hodgkin's Lymphoma During Pregnancy
Hypopharyngeal Cancer
Hypothalamic and Visual Pathway Glioma, Childhood
Intraocular Melanoma
Islet Cell Carcinoma (Endocrine Pancreas)
Kaposi's Sarcoma
Kidney (Renal Cell) Cancer
Kidney Cancer, Childhood
Laryngeal Cancer
Laryngeal Cancer, Childhood
Leukemia, Acute Lymphoblastic, Adult
Leukemia, Acute Lymphoblastic, Childhood
Leukemia, Acute Myeloid, Adult
Leukemia, Acute Myeloid, Childhood
Leukemia, Chronic Lymphocytic
Leukemia, Chronic Myelogenous
Leukemia, Hairy Cell
Lip and Oral Cavity Cancer
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis Fungoides and Sézary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer -continued Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma
Pregnancy and Breast Cancer
Pregnancy and Hodgkin's Lymphoma
Pregnancy and Non-Hodgkin's Lymphoma
Primary Central Nervous System Lymphoma
Prostate Cancer
Rectal Cancer
Renal Cell (Kidney) Cancer
Renal Cell (Kidney) Cancer, Childhood
Renal Pelvis and Ureter, Transitional Cell Cancer
Retinoblastoma
Rhabdomyosarcoma, Childhood
Salivary Gland Cancer
Salivary Gland Cancer, Childhood
Sarcoma, Ewing's Family of Tumors
Sarcoma, Kaposi's
Sarcoma, Soft Tissue, Adult
Sarcoma, Soft Tissue, Childhood
Sarcoma, Uterine
Sezary Syndrome
Skin Cancer (non-Melanoma)
Skin Cancer, Childhood The aforementioned cancer cells may also serve as target cells for the delivery method of the invention, which comprises administering to the cell in vitro or in vivo a molecular conjugate of the invention. Thus, in some embodiments, the conjugate is administered to a cancer cell in vitro or in vivo. The conjugate may be administered to the cells with a pharmaceutically acceptable carrier within a composition of the invention and, optionally, administered with one or more additional agents.

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site. The term "tumor" is inclusive of solid tumors and non-solid tumors. The conjugates and compositions of the invention can be administered locally at the site of a tumor (e.g., by direct injection) or remotely. In some embodiments, the conjugate or composition is administered to the subject systemically, e.g., intravascular, such as intravenous administration.

To treat a disease according to an embodiment of the invention, a receptor antagonist can be selected for its capability to bind to all or most of the target cells in a subject without binding to all or most of the non-target cells. For example, to treat a cancer according to the current invention, the receptor antagonist can be selected for its capable of binding to most or all of the cancer cells without binding to most or all of the normal cells through a receptor specific for cancer cells.

In some embodiments, the antagonist is a delta opioid receptor (DOR) ligand antagonist (for example, DMT-Tic such as DMT-Tic-OH or DMT-Tic-Ala-OH), which may be used for delivery to lung cancer cells or treatment of lung cancer; or an MCR1 ligand antagonist, which may be used for delivery to melanoma cells or treatment of melanoma.

The subjects that can be treated according to the methods of the current invention can be a human or non-human animal. For example, the subject can be a human, non-human primate, pig, dog, rodent, feline, bovine, or other mammal. As used herein, the terms "subject" and "patient" are used interchangeably. Likewise, the conjugates and compositions can be administered to human cells or non-human animal cells in vitro or in vivo. In some embodiments, the cells are mammalian cells.

The pharmaceutically effective amount of the conjugate depends on the type of disease to be treated, type of receptor antagonist and the immune effector conjugated to the antagonist as well as the tolerance of the subject for the treatment.

The disease treatment according to the current invention can also be administered alone or in combination with one or more other treatments. For example, cancer in a subject can be treated by administering the molecular conjugate of the current invention in combination (simultaneously or consecutively) with chemotherapy and/or radiotherapy. For some diseases, treatment of the subject may include surgery. The conjugate may be administered before or after surgery.

As used herein, the terms "treat" or "treatment" refer to both therapeutic treatment and prophylactic or preventative measures, wherein the object is to prevent or slow down (lessen) an undesired physiological change or disorder, such as the development or spread of an oncological disorder (e.g., cancer). In some embodiments, the subject has a cancer at the time of administration. In other embodiments, the subject does not have a cancer at the time of administration, in which case the conjugate of the current invention may be administered to prevent or delay onset of the cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. In some embodiments, the treatment methods include identifying the subject as having cancer or another disease or disorder to be treated.

The amount of conjugate administered to the subject or cell may be an effective amount, e.g., a therapeutically effective amount. As used herein, the term "(therapeutically) effective amount" refers to an amount of an agent (e.g., a conjugate of the invention) effective to treat a disease or disorder in a subject. In the case of cancer, the therapeutically effective amount of the agent may directly or indirectly (e.g., through an immune response) reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer. To the extent the agent may prevent growth and/or kill existing cancer cells, it may be cytostatic and/or cytotoxic. For cancer therapy, efficacy can, for example, be measured by assessing the time to disease progression (TTP) and/or determining the response rate (RR).

While conjugates of the current invention can be administered as isolated compounds, these compounds can also be administered as part of a pharmaceutical composition. The subject invention thus further provides compositions comprising one or more conjugates of the current invention in association with at least one pharmaceutically acceptable carrier. Conjugates and compositions containing them can be administered to a subject locally at or adjacent to a site of intended action (e.g., a tumor or lesion), or systemically (e.g., intravascularly). The conjugate and pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

Optionally, the antagonists and/or immune effector molecules of the conjugates, and suitable bioactive agents that are optionally administered with the conjugates separately or within the same formulation, can be formulated as pharmaceutically acceptable salts or solvates.

Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of compounds may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Specifically identified receptor antagonists, immune effectors, and bioactive agents can be substitutes with an analog.

As used herein, the term "analog" refers to an agent which is substantially the same as another agent but which may have been modified by, for example, adding side groups, oxidation or reduction of the parent structure. Analogs of receptor antagonists, immune effectors, and other bioactive agents disclosed herein, can be readily prepared using commonly known standard reactions. These standard reactions include, but are not limited to, hydrogenation, alkylation, acetylation, and acidification reactions. Chemical modifications can be accomplished by those skilled in the art by protecting all functional groups present in the molecule and deprotecting them after carrying out the desired reactions using standard procedures known in the scientific literature (Greene, T. W. and Wuts, P. G. M. "Protective Groups in Organic Synthesis" John Wiley & Sons, Inc. New York. 3rd Ed. pg. 819, 1999; Honda, T. et al. *Bioorg. Med. Chem. Lett.*, 1997, 7:1623-1628; Honda, T. et al. *Bioorg. Med. Chem. Lett.*, 1998, 8:2711-2714; Konoike, T. et al. *J. Org. Chem.*, 1997, 62:960-966; Honda, T. et al. *J. Med. Chem.*, 2000, 43:4233-4246; each of which are hereby incorporated herein by reference in their entirety). Analogs, fragments, and variants of the receptor antagonists, immune effectors, and bioactive agents exhibiting the desired biological activity can be identified or confirmed using cellular assays or other in vitro or in vivo assays.

In some cases, a receptor antagonist, immune effector, or bioactive agent may be a polypeptide.

In some cases, a receptor antagonist, immune effector, or bioactive agent may be an antibody or antigen-binding portion thereof. Optionally, the antibody may be a human antibody or humanized antibody, or antigen-binding portion thereof.

The terms "immunoglobulin" and "antibody" (used interchangeably herein) include a protein having a basic four-polypeptide chain structure consisting of two heavy and two light chains, said chains being stabilized, for example, by interchain disulfide bonds, which has the ability to specifically bind an antigen (e.g., DOR, PD-1, or PD-L1). The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind an antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable," based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions." The "constant" domains of an antibody light chain are referred to interchangeably as "light chain constant regions," "light chain constant domains," "CL" regions or "CL" domains. The "constant" domains of an antibody heavy chain are referred to interchangeably as "heavy chain constant regions," "heavy chain constant domains," "CH" regions or "CH" domains). The "variable" domains of an antibody light chain are referred to interchangeably as "light chain variable regions," "light chain variable domains," "VL" regions or "VL" domains). The "variable" domains of an antibody heavy chain are referred to interchangeably as "heavy chain constant regions," "heavy chain constant domains," "VH" regions or "VH" domains).

Immunoglobulins or antibodies can exist in monomeric or polymeric form, for example, IgM antibodies which exist in pentameric form and/or IgA antibodies which exist in monomeric, dimeric or multimeric form. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) *Clin. Exp. Immunol.* 79:315-321; Kostelny et al., (1992) *J. Immunol.* 148:1547-1553.

The term "antigen-binding portion" of an antibody (or "antibody portion") includes fragments of an antibody that retain the ability to specifically bind to an antigen (e.g., DOR, PD-1, or PD-L1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P. et al., (1993) *Proc. Natl. Acad. Sci. USA* 90:6444-6448; Poljak, R. J. et al., (1994) *Structure* 2:1121-1123). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M. et al., (1995) *Human Antibodies and Hybridomas* 6:93-101) and use of a cysteine residue, a marker peptide and a C-terminal polyhistidine tag to make bivalent and biotinylated scFv molecules (Kipriyanov, S. M. et al., (1994) *Mol. Immunol.*, 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. Preferred antigen binding portions are complete domains or pairs of complete domains.

"Specific binding," "specifically binds," "specific for", "selective binding," and "selectively binds," as used herein, mean that the compound, e.g., antibody or antigen-binding portion thereof, exhibits appreciable affinity for a particular antigen or epitope and, generally, does not exhibit significant cross-reactivity with other antigens and epitopes. "Appreciable" or preferred binding includes binding with an affinity of at least $10^6$, $10^7$, $10^8$, $10^9$ $M^{-1}$, or $10^{10}$ $M^{-1}$. Affinities greater than $10^7$ $M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{10}$ $M^{-1}$, preferably $10^7$ to $10^{10}$ $M^{-1}$, more preferably $10^8$ to $10^{10}$ $M^{-1}$. An antibody that "does not exhibit significant cross-reactivity" is one that will not appreciably bind to an undesirable entity (e.g., an undesirable proteinaceous entity). For example, in one embodiment, an antibody or antigen-binding portion thereof, specifically binds to a cell surface receptor, such as, for example, the delta opioid receptor (DOR), but will not significantly react with other non-DOR receptors. Specific or selective binding can be determined according to any art-recognized means for determining such binding, including, for example, according to Scatchard analysis and/or competitive binding assays.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The term "human antibody" includes antibodies having variable and constant regions corresponding to human germline immunoglobulin sequences as described by Kabat et al. (See Kabat, et al., (1991) *Sequences of proteins of Immunological Interest, Fifth Edition*, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In a preferred embodiment, these replacements are within the CDR regions as described in detail below.

The term "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D. et al., (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences (See Kabat E. A., et al., (1991) *Sequences of Proteins of Immunological Interest, Fifth Edition*, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

In some cases, a receptor antagonist, immune effector, or bioactive agent may be a small molecule. For example, a small molecule can have a molecular weight of about any of 100 to 20,000 daltons, 500 to 15,000 daltons, or 1000 to 10,000 daltons.

The conjugates of the current invention can be formulated according to known methods for preparing pharmaceutically useful compositions. Formulations are described in a number of sources which are well known and readily available to those skilled in the art. For example, *Remington's Pharmaceutical Science* (Martin 1995) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

As used herein, the terms "cell" and "cells" are used interchangeably herein and are intended to include either a single cell or a plurality of cells unless otherwise specified.

As used herein, the term "anti-cancer agent" refers to a substance or treatment that inhibits the function of cancer cells, inhibits their formation, and/or causes their destruction in vitro or in vivo. Examples include, but are not limited to, cytotoxic agents (e.g., 5-fluorouracil, TAXOL) and anti-signaling agents (e.g., the PI3K inhibitor LY).

As used herein, the terms "polypeptide", "peptide", and "protein" are used interchangeably to refer to polymers of any length comprising amino acid residues linked by peptide bonds (e.g., peptide antagonist).

Following are examples which illustrate procedures for practicing the invention. These examples should not be construed as limiting. All percentages are by weight and all solvent mixture proportions are by volume unless otherwise noted. It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Example 1—LHRH Antagonist Conjugated to Immune Effectors to Treat Breast Cancer

An embodiment of the current invention provides an LHRH antagonist, Cetrorelix, conjugated to human recombinant CD86, 41BBL, or OX40L ectodomain as a therapeutic agent for treatment of breast cancer. The FDA-approved LHRH antagonist, Cetrorelix, is connected via a trifunctional linker to VivoTag 680 and to an amine reactive site for coupling with primary amines on the surface of the commercially available human recombinant CD86, 41BBL, or OX40L ectodomain. The binding and the timing of uptake of the Cetrorelix conjugated to VivoTag 680 with and without the immune effector conjugates with LHRH positive (MDA-MB-231 and HCC1806) and LHRH-R siRNA knocked down MB-231 cells using in vitro fluorescence microscopy studies verifies LHRH binding affinity and specificity. Those same human cell lines can be used for in vitro immune activation assays. Untreated and treated groups (Cetrorelix, each cetrorelix construct alone, CD86+41BBL, 41BBL+ OX40L, and all three constructs) of CFSE labeled target cells can be co-cultured with tumor cell lysate educated HLA matched T cells (5:1 target/effector) overnight. Supernatants can be taken for cytometric bead assays for IL-2 and IFN γ cytokines. Cell-mediated cytotoxicity flow assays using CFSE/7AAD can be used to measure proportion of live/dead target cells.

From the extensive studies designed to deliver cytotoxic agents to LHRH expressing tumors, there is a deep understanding of the critical pharmacophores of the LHRH ligands and so we can use this information to select LHRH ligand attachment sites that do not interfere with LHRH ligand binding with its receptor. There are numerous LHRH agonists and antagonists that have been reported, many have undergone clinical safety and efficacy studies, and several have gained full regulatory approval. This embodiment of the current invention focuses on LHRH antagonists rather than LHRH agonists because they bind the LHRH receptor but block its activation and they do not undergo rapid endocytosis like the LHRH agonists. While others have focused on the use of LHRH agonists to deliver cytotoxic agents into targeted tumor cells, LHRH antagonist-immune effector conjugates stay outside the targeted tumor cells are favored based on the teachings of the current invention. The display of covalently attached immune effectors near the exterior surface of the targeted tumor cells stimulates a strong immune response within the tumor microenvironment. One or multiple copies of the LHRH antagonist ligand relative to immune effector(s) may be more effective and therefore, a skilled artisan can compare relative stoichiometries to determine which has the best overall specificity and localized immune response in vitro. Any of the LHRH antagonists are readily prepared and conjugated. An example is Cetrorelix, which is the FDA-approved LHRH antagonist with the least esoteric amino acids, and is less costly to synthesize. Other LHRH antagonists are described in Jyothi Thundimadathil, Cancer treatment using peptides: current therapies and future prospects, *Journal of Amino Acids*, Volume 2012: Article ID 967347, the contents of which are herein incorporated by reference in its entirety, particular, Table 1 on page 3. These antagonists include but are not limited to Abarelix, Cetrorelix, Degarelix and Genirelix.

The cytotoxic deliver strategies using the LHRH agonists have exclusively used the sixth residue which is usually D-lysine epsilon nitrogen as the attachment site and a structure-activity relationship analysis of the LHRH-antagonists also shows that significant variation of the sixth residue is tolerated without loss of LHRH antagonist activity. Thus, the D-citrulline in the FDA-approved LHRH antagonist cetrorelix can be substituted with a D-ornithine to produce an amide linkage to a trifunctional linker shown in FIG. 1.

FIG. 1 shows proposed synthesis of LHRH antagonist conjugates with a fluorescent imaging agent and immune effectors.

Standard Fmoc-solid phase peptide synthesis (SPPS) methods have been used to prepare cetrorelix and can be used for the synthesis of the alloc-protected-D-ornithine analog shown above as the resin-bound starting material. Alloc orthogonal protection scheme can be used for specific labeling of peptides. The length of the linker can be optimized to maximize LHRH targeting while keeping the overall MW as low as possible to simplify the purification and characterization of the conjugates. Short and progressively longer molecularly defined PEG diacids are commercially available from Quanta Biodesign and can be used to react with the free amine of the cetrorelix analog. This linker coupling in Step 6 while still on resin makes it very unlikely that two different cetrorelix analogs will be coupled to either ends of the same linker due to the pseudo dilution effect and it enables easy separation and reuse of any unreacted linker diacid. The unreacted carboxylic acid on the other end of the linker in Step 8 will be activated to form a stable NHS activated ester and cleaved from resin just before it is to be used for reaction with the immune effectors. The reactions with the immune effectors can be done in aqueous media buffered to enhance specific coupling to lysines on the surface of the immune effectors. The relative stoichiometry can be controlled to favor 1:1 and 4:1 cetrorelix-immune effector ratios and can be used determine the preferred relative stoichiometry. This is unlikely to have any significant effect on LHRH antagonist binding affinity and if such binding affinity is changed, other options including N- or C-terminal extension strategies can be used.

The conjugation of the Cetrorelix-VivoTag 680 with the immune effectors is designed to be similar to other known protein tagging strategies, such as fluorescent tags or pegylation strategies. There are structurally required disulfide linkages in the ectodomains of the immune effector recombinant proteins and so we think it is unwise to attempt any strategies that involve attempts to reduce and alkylate those cysteine residues. For example, a selective reaction with the lysine epsilon nitrogens in a buffered aqueous buffer can be used. There are thousands of successful examples using this type of approach involving an activated ester reaction with random lysines on the protein surface and this strategy is the basis for numerous protein-tagging kits.

Example 2—Enhancing Immunotherapy by Targeting Immune Effectors to Ovarian Cancers Expressing LHRH This embodiment of the invention provides a highly innovative strategy to deliver immunotherapy to subjects with ovarian cancer. This embodiment can dramatically enhance the efficacy of immunotherapy by delivering immune effectors to ovarian cancer cells in a highly efficient and targeted manner using the LHRH targeting approach. Due to high expression of LHRH in ovarian cancers, OVCA is an excellent model to explore this highly innovative and novel approach to targeted solid tumor immunotherapy.

Other cancers that can also be targeted using the LHRH ligand immune targeting approach include prostate, breast, endometrial, and pancreatic cancers. This approach is likely to reduce or eliminate the dose-limiting adverse immune responses seen with systemic immunotherapy approaches and make it safe to use combinations of strong immune stimulators that cannot currently be used safely in standard of care immunotherapy approaches.

The LHRH antagonist, Cetrorelix, can be conjugated to a series of molecules that can enhance T cell infiltration and activation to determine which combination can induce the most profound T cell responses to ovarian cancers in vitro.

This embodiment of the invention also provides methods of conjugating costimulatory molecules such as CD40L and 41BB as well as chemokines and cytokines such as CCL21 and IL-12 that have been shown to enhance the activation of anti-tumor T cells. The duration of the immune response can be determined to allow an estimate for the timing of additional doses to maintain an enhanced immune response.

Example 3—Enhancing Immunotherapy by Targeting Immune Effectors to Cancers Expressing Delta Opioid Receptor (DOR)

This embodiment of the current invention provides innovative strategies for prevention and treatment of early and/or localized lung cancer. This embodiment provides an immunotherapy by specifically delivering immune effectors to lung tumors that express the delta opioid receptor (DOR) using the well-known DOR ligand targeting approach. A majority of non-small cell lung cancer cancers (NSCLC) express greater DOR than normal lung tissues. As such, this embodiment focuses on the delivery of immune effectors to NSCLC. This approach will yield therapies that can safely and effectively enhance the immune response to the lung cancer and potentially lead to complete clinical responses.

There are several targeting ligands from which to choose, but the delta opioid receptor (DOR) ligand antagonist Dmt-Tic is the subject of this Example, as the antagonist of a cell surface receptor specific to a target cell (also referred to herein as a targeting ligand) [34]. By immunohistochemistry of patient samples the inventors have shown that 73% of NSCLC express DOR with no expression in normal lung or other tissues of concern. NSCLC is the most common lung cancer and lung cancer causes more deaths than the next 4 most common cancers combined. DOR has extensive CNS expression [35], but those receptors are not imaged due to the impermeable blood brain barrier (BBB) [36,37]; therefore, the inventors anticipate that none of the even larger DOR-TTMs will reach DORs in the CNS.

There are many known T cell modulator ligands, which can be utilized as immune effectors in the invention for NSCLC and other diseases. Targeting of anti-PD1 and anti-PDL1 can be used as reagents to alleviate inhibition of the immune system in the tumor. The inventors also propose to target murine CD137, OX40, and CD28 with the murine ectodomains of CD137L, OX40L, and CD86 to determine if T cell activators can be made safer due to the delivery and concentration in the tumor relative to normal tissues. These experiments with anti-PD1 and anti-PDL1 will be with the murine antibodies and the murine T cell activators will use the natural ectodomains except that the inventors will mutate all of the existing lysines to arginines and then add 1 or 4 lysines at the N-termini of each of these ectodomains to enable easy and selective conjugation with the targeting ligand-linker conjugate.

The inventors will verify that these untargeted T cell modulators activate T cells in in vitro assays and in an established immune competent murine lung cancer model and then the DOR-TTMs will be compared to test the hypothesis that these targeted-analogs will concentrate at the targeted tumors and give greater immune activation within the tumor microenvironment with lower systemic doses. This DOR-targeting strategy will open the field to targeting of other T cell modulator ligands, T cell modulator antibodies, and T cell modulator antibody fragments with this targeting ligand and with other established targeting ligands for other cancers. For instance, the CD137 agonistic antibody (CD137AA) is a powerful T cell costimulatory agent that has efficacy in clinical trials, but immune-related adverse events limit its potential use, the proposed targeting could make this potential immunotherapy drug safer and more effective [38-40].

The experiments described herein will confirm that targeting TTMs with Dmt-Tic will concentrate the T cell activation within the lung tumor microenvironment. The inventors will compare untreated survival, with the untargeted TTMs and with the targeted analog(s) treatment, to determine if the targeting significantly lowers the systemic doses needed for similar activity in an immune competent murine lung tumor model.

A. Conjugation of Dmt-Tic with a Vivo Tag 680 Dye to Allow Confocal Microscopy and In Vivo Imaging Dmt-Tic will be conjugated with a Vivo Tag 680 dye to allow confocal microscopy and in vivo imaging. This conjugate will be coupled via a Peg linker with a normal murine IgG, murine anti-PD1, murine anti-PDL1 and the slightly modified murine ectodomains of CD137L, OX40L, and CD86. Dmt-Tic Vivo Tag 680 dye adducts are known to maintain sub-nanoM Kd binding affinity with DOR on the cell surface and the Peg linker length will be optimized as needed to maintain that binding affinity and specificity. The immune activation of T cells will be compared with untargeted T cell modulators and the Dmt-Tic-Vivo Tag 680-TTMs and the linker will be optimized to maintain the highest possible in vitro T cell modulator activity. It is typical for peptides or proteins to work as modular components because these molecules have multiple conjugation sites that maintain the bioactivity of the individual components following conjugation.

The DOR specific ligand [34], N,N-dimethyl-Dmt-Tic-Lys, will be connected via a trifunctional linker to Vivo Tag 680 Dye (Perkin Elmer) and to an amine reactive site for coupling with primary amines on the surface of commercially available murine anti-PD1 and anti-PDL1, and the ectodomains for CD137L, OX40L, and CD86. The precursors and the final conjugates will be characterized using LC-MS and MALDI-TOF MS experiments.

The inventors will use murine cell lines that express DOR, those in which human DOR will be ectopically expressed, and an established whole-cell time-resolved fluorescence-binding assay to determine the binding affinities of the conjugates [34]. The timing of cellular binding and uptake will be determined using live-cell epifluorescence microscopy. The same cell lines will be used for in vitro immune activation assays (LKR-13).

The alloc-protected N, N-dimethyl-Dmt-Tic-Lys will be synthesized on Tentagel resin with the Rink amide linker using the commercially available amino acid building blocks followed by on resin reductive amination, as shown in FIG. 2A. The alloc group can then be selectively deprotected giving the free lysine as the only reactive species, and another lysine-based linker and commercially available peg-di-acids can be coupled. The inventors will use the longest molecularly defined PEG-diacid activated esters that are commercially available (the 28 carbon and oxygen atoms end to end has acceptable purity). If that linker retains high affinity and specificity to DOR, the conjugate will be cleaved from the resin using TFA and coupled with commercially available murine T cell modulators, and HPLC will be used purify the products.

B. Use of Dmt-Tic-Vivo Tag 680-Normal Murine IgG and its Targeted T Cell Modulators (TTMs) to Measure the Dosages and Dosage Timing Dmt-Tic-Vivo Tag 680-normal murine IgG and its TTMs will be used to measure the dosages and the timing of repeat dosages that bind the targeted DOR expressing cells in vitro using confocal microscopy, intravital confocal microscopy, and in vivo imaging in mice that express normal levels of human DOR on the murine lung tumors. Biodistribution studies will determine the tumor retention and systemic clearance profile of the lead agents.

Targeted tumor uptake and retention of the Dmt-Tic-VivoTag-680-TTM will be carried out in mice bearing DOR-expressing LKR subcutaneous (s.c.) and lung orthotopic (o.t. tumors in mice syngeneic for these tumors 129/SvJaeJ). Tumor uptake and retention, pharmacokinetics (PK) of systemic clearance and biodistribution (BD) of these conjugates will be measured to predict the overall exposure of the tumor-bearing animals and to optimize dosing amounts and dosing intervals. The full antibody TTMs will likely have a significantly longer circulating half-life than the ectodomain-based analogs, and the ectodomains analogs may allow more frequent dosing.

Tumor selectivity, PK, and BD will be determined by generating LKR subcutaneous tumors in C57BL/6 mice and tumor specificity of Dmt-Tic-VivoTag-680-TTM will be demonstrated via blocking studies using the unlabeled Dmt-Tic-inactive protein. These conjugates will be selected to have no significant immunogenicity in mice and will have similar circulating half-lives compared to the murine Dmt-Tic-TTM conjugates. These initial imaging studies will involve a series of post-intravenous (i.v.) administration image acquisitions using the FMT 2500 fluorescence tomography imaging system (PerkinElmer) over a time-course that encompasses tumor and systemic uptake and clearance. The initial imaging studies will be used to inform subsequent PK and BD studies for the lead constructs that will involve i.v. injection of agent followed by imaging, humane euthanization and extraction of blood, liver, spleen, kidneys, brain, heart, lung, muscle, small bowel and tumors at a series of time-points that encompass the tumor uptake and tumor and systemic clearance profiles. FMT 2500 fluorescence image acquisitions will be made prior to euthanization and high-resolution fluorescence images will be acquired of the removed tissues for each mouse using the IVIS 200 imaging system (PerkinElmer). All animal-imaging studies will be conducted using 5 animals per group, as past experience and power analyses have demonstrated that these numbers are suitable for these in vivo studies.

To determine the in vivo cell-surface accumulation of the lead Dmt-Tic-TTM conjugates and T-cells in tumors, intravital imaging will be performed as previously described [29] using dorsal window chambers mounted on C57BL/6 mice with B16-F10 tumor xenografts implanted under the glass cover. Following administration of VivoTag 680 conjugates and/or green Qtraker cell labeled T cells (Invitrogen), intravital imaging will be performed by mounting the anesthetized mouse on the stage of a confocal microscope and imaging at a series of post-administration time points [29].

LKR-13 with human DOR expression will be prepared, cell binding assays, in vivo cell imaging, dorsal window imaging, T cell aggregation studies, and post-treatment imaging will be completed.

C. Treatment of Animals with Dmt-Tic-Vivo Tag 680-Normal Murine IgG, Dmt-Tic-Vivo Tag 680-TTMs, and Non-Targeted T Cell Modulator Dmt-Tic-Vivo Tag 680-normal murine IgG, Dmt-Tic-Vivo Tag 680-TTMs, and non-targeted T cell modulator treated animals will be dosed at 0, 50, 100, 300 μg/kg every 14 days for 7 cycles via tail vein I.V. and the animals will be monitored for anti-tumor activity and survival advantage for 150 days.

The in vivo activity of Dmt-Tic-VivoTag-680-TTM in the animal models used above to obtain a statistically significant tumor growth reduction, and enhancement of T cell activation and tumor microenvironment immunogenicity relative to untreated animals and determine if 7 doses are tolerated and effective in immune competent murine models.

In previous studies, the inventors found that anti-PD1 (3 injections at 300 μg/kg) generates a highly significant anti-tumor response in the LKR model. Dmt-Tic-VivoTag-680-non-targeting protein, Dmt-Tic-VivoTag-680-TTM, and non-targeted VivoTag-680-TTM treated animals will be dosed at 0, 50, 100, or 300 μg/kg every 14 days for 7 cycles via tail vein I.V. and the animals will be monitored for adverse immune-related events and for survival advantage for 150 days. For this study, the inventors will generate LKR subcutaneous (s.c.) and 1 lung orthotopic (o.t. tumors in mice syngeneic for these tumors 129/SvJaeJ. Starting on day 14 (s.c.) or day 7 (o.t.) after tumor injection, mice will be treated with a range of 50-300 μg/mouse, with the expectation that lower amounts will show comparable efficacy to a higher dose of untargeted TTM with a timing determined by the BD properties determined (as described above) of the optimized Dmt-Tic-VivoTag-680-TTM. Control mice will receive no treatment, Dmt-Tic-VivoTag680-inactive protein or VivoTag-680-TTM alone. Tumors will be measured every 2-3 days with Vernier calipers, and the largest perpendicular measurements of tumor area (in mm$^2$) will be recorded. Data will be reported as the average tumor area+/−SE, with 8 mice per group. Standard survival experiments will also be incorporated into the overall study plan whereby in additional experiments the percentage of surviving mice will be recorded over time.

T cell activation in vitro cell culture will be conducted by measuring IFNg and TNFa. T cell activation in tumors will be determined by isolating TIL and measuring IFNg and TNFa and until all the constructs are prepared, enhancement of tumor microenvironment immunogenicity will be measured by T cell produced cytokines will be determined through induction of IFNg-induced T cell chemokines and increased infiltration of T cells after treatment relative to controls will be carried out. Additional lung tumor models such as 344SQ may be used.

Figures 2A, 2B:
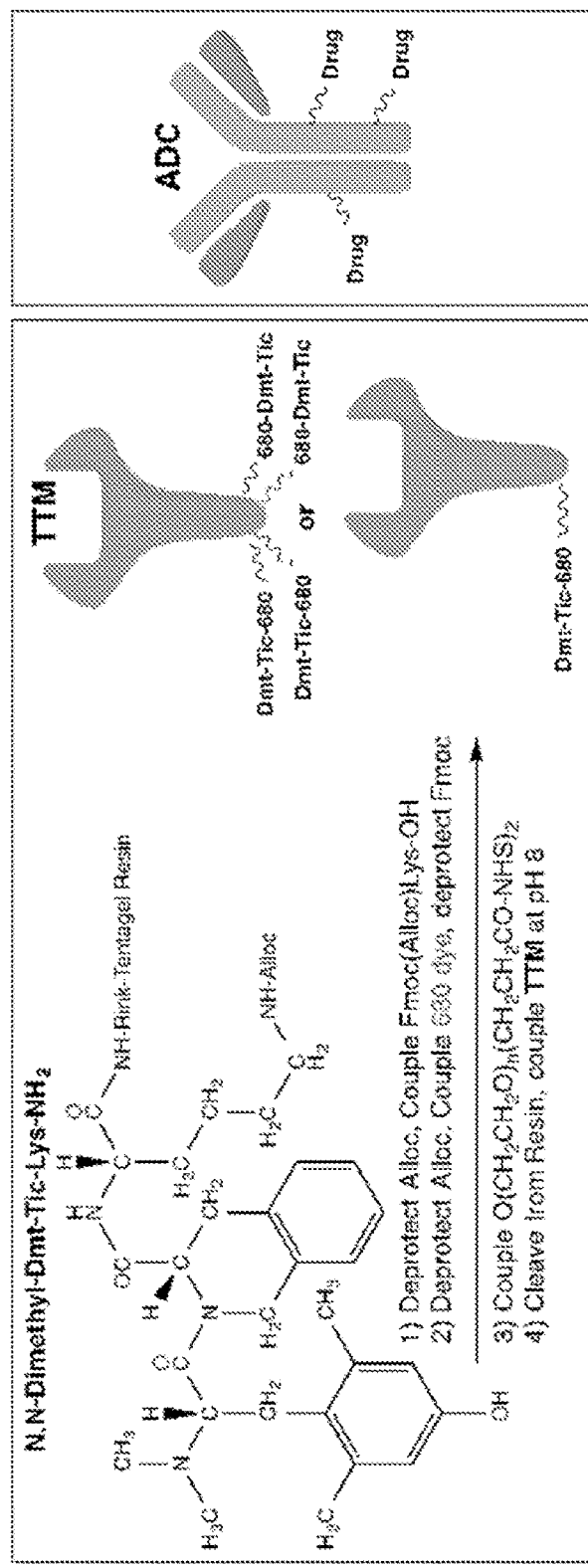
FIGS. 2A and 2B.

Targeted versions of T cell modulators will greatly enhance the safety and effectiveness of T cell modulators including T cell activators that heretofore have been too toxic for regulatory approval. FIG. 2A shows exemplified embodiments in which Dmt-Tic is utilized as a DOR specific ligand antagonist and three known T cell activation modulator ligands as immune effectors. However, this targeting ligand (Dmt-Tic) may be used in conjunction with different T cell modulators; likewise, different targeting ligands may be used with the same and other T cell modulator ligands. These TTMs may be compared to antibody-drug conjugates (ADCs) shown in FIG. 2B.

Figures 3A, 3B, 3C, 3D, 3E, 3F:
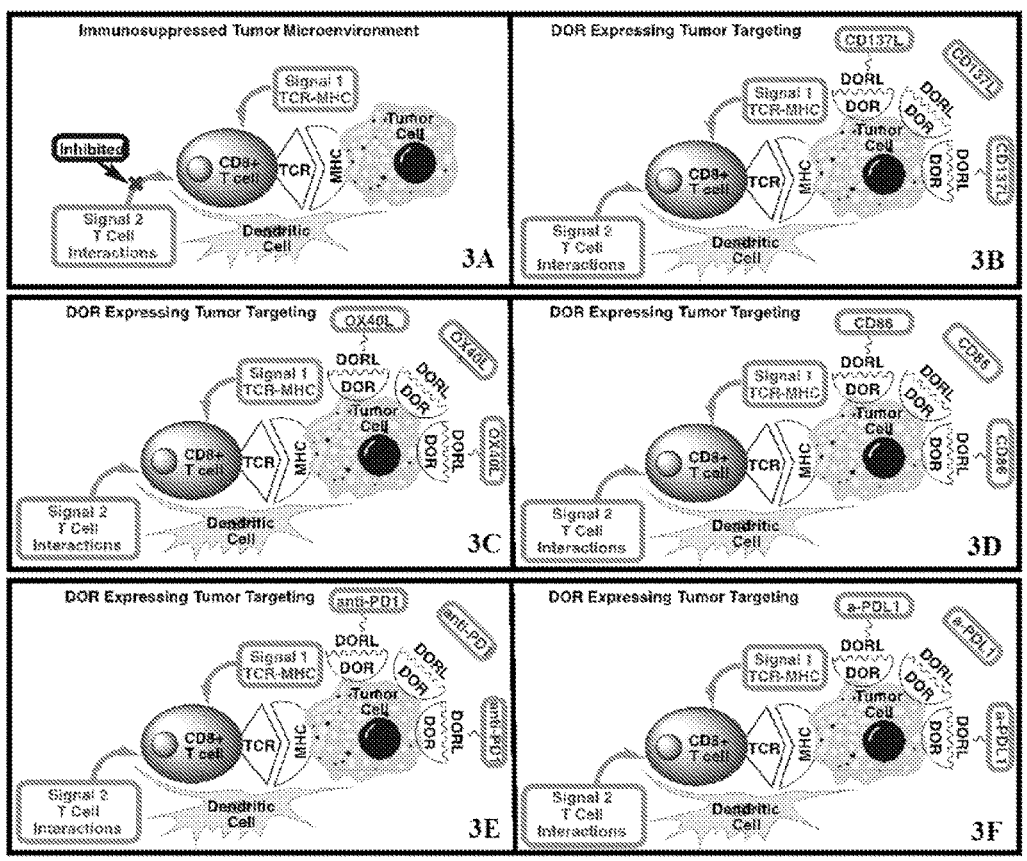
FIGS. 3A-3F.

FIG. 3A represents an immunosuppressed tumor microenvironment. The primary activation signal for a T cell is binding of the T cell receptor (TCR) to a major histocompatibility complex (MHC) loaded with a target antigen. This is insufficient for complete activation and full activation requires secondary signals on the T cell. The tumor microenvironment can be immunosuppressed by PD1-interaction with PDL1 or a lack of sufficient T cell costimulatory interactions like the CD137-CD137L, OX40-OX40L, or CD28-CD86 or any of the other receptors and ligands that modulate T cell and other immune effector cell interactions in the tumor microenvironment [40-42]. When the primary signal from the TCR-MHC interaction and one or more secondary signals are engaged simultaneously, it results in greater T cell activation. Coating the surface of tumor cells with TTMs is expected to result in enhanced activation and survival of T cells among the tumor infiltrating lymphocytes and eradication of tumor cells via perforin/granzyme cytolytic T lymphocyte (CTL) killing. This approach can make cancer immunotherapy safer and more effective for cancers that can be targeted.

FIGS. 3B-3F show some of the targeted Dmt-Tic-TTMs that can be prepared to illustrate the potential breadth of this targeting strategy. By coating the outside of the targeted tumor with TTMs, a greater number of fully activated T cells should concentrate at the targeted tumor. There are other targeting ligands for different cancer types [21,25,43], which are each incorporated herein by reference in their entirety. This effect is expected to be dose-dependent; sub-therapeutic doses should concentrate to therapeutic dose levels at the tumor and fully activated T cells will not continue to receive these enhanced immune activation signals as they diffuse away from the targeted tumor microenvironment because of the very limited DOR expression on other normal tissues that are accessible to the conjugate. This approach can revolutionize cancer immunotherapy treatment for cancers that can be targeted.

The inventors have designed the imaging and biodistribution (BD) studies to guide efforts to optimize dosing intervals to keep an effective amount of Dmt-Tic-TTMs occupying the DOR receptors in the lung tumor microenvironment. It may be determined that an initial bolus dose works fine, but we want to keep the Dmt-Tic-TTMs at effective concentrations in the tumor, while the unbound Dmt-Tic-TTMs remains at less than effective concentrations.

It is possible that a combination of different Dmt-Tic-TTMs will work better than any one Dmt-Tic-TTM as seen when anti-CTLA4 and anti-PD1 are combined [33], or that sequential treatment with the one Dmt-Tic-TTM followed by a different Dmt-Tic-TTM is more effective or a safer way of activating the immune response in the tumor microenvironment.

Due to tumor heterogeneity, it may be that not every cell in the tumor will highly express a targeted receptor or have the same antigens, but it is known that quorums of activated T cells kill much more target cells than there are T cells in the quorum, and so cells throughout the tumor microenvironment are killed, not just the nearest neighbor tumor cells that express the targeted receptor. This activated CTL process also activates other tumor infiltrating lymphocytes (TILs) and new antigens that are processed by antigen presenting cells go on to produce additional T cells that respond to additional antigens via a process called epitope spreading [44-47]. These phenomena are likely responsible for the durable complete responses seen with the untargeted systemically administered checkpoint inhibitors, and the Dmt-Tic-TTMs are likely to promote the same effects, but with a more targeted focus on the tumor microenvironment.

DOR is expressed on lung cancer but not on normal lung cells and is thus an important biomarker for lung cancer. There is abundant evidence that Dmt-Tic can be conjugated with various linkers and imaging probes (imaging agents) and the resulting Dmt-Tic conjugates maintain very high binding affinity and specificity for DOR-expressing cells and tumors. Dmt-Tic analogs have about 3 nM binding affinity for DOR-expressing cells and so the targeting ligand probably has greater binding affinity for its target than T cell modulators have for their targets on the surface of T cells [34]. DOR is expressed in the central nervous system (CNS), but the blood brain barrier (BBB) prevents Dmt-Tic imaging probes from reaching those sites and so no CNS imaging is seen with those imaging probes and the Dmt-Toc-TTMs are even less likely to breach the BBB [34,37]. Varying the ratio of Dmt-Tic to the TTM may be utilized to increase the avidity of the conjugate for the targeted lung cancer cells.

Conjugates with an average of one Dmt-Tic targeting ligand per TTM will be compared with an average of four Dmt-Tic targeting ligands per TTM to see if the added targeting ligand leads to higher lung cancer cell specific binding avidity and determine if higher binding avidity decreases the dose of the conjugate needed for the desired bioactivity. It is important that Dmt-Tic is an antagonist. It will antagonize the signaling that the lung cancer cells use to enhance proliferation. Therefore, it will be helpful to compare Dmt-Tic-linker-fluorescent tag conjugated with an inactive protein with the fully active conjugate. Dmt-Tic antagonists are not internalized rapidly like DOR agonists; therefore, it desirable to coat the exterior cell membranes of targeted tumor cells with the Dmt-Tic-TTM conjugate and thereby concentrate and activated T cells in the tumor microenvironment. Agonist targeting ligands can promote internalization of conjugated cargo within minutes and if that occurs, the T cell activation modulator is not likely to function as effectively. Antagonist targeting ligands remain outside of targeted cells for hours or days.

There are bispecific antibodies called bispecific T cell engagers (BiTEs) that use one of the molecular recognition elements to target a cancer and another molecular recognition element of the antibody to promote T cell activation and this class of bispecific antibodies are potent T cell activators, but no BiTEs have won regulatory approval so far [16,52, 53]. Selecting targeting ligands that are already known, the ability to conjugate multiple copies of the targeting ligand to optimize binding avidity, and the ability to label the synthetic targeting ligands with a detectable moiety (e.g., an imaging probe) can make molecular conjugates of the invention easier to prepare and optimize than BiTEs.

All patents, patent applications, provisional applications, and publications referred to or cited herein are incorporated by reference in their entirety, including all figures and tables, to the extent they are not inconsistent with the explicit teachings of this specification.

Exemplified embodiments of the invention include, but are not limited to:

1. A molecular conjugate comprising:
   a) an antagonist of a cell surface receptor specific to a target cell; and
   b) an immune effector conjugated to the antagonist.
2. The molecular conjugate of embodiment 1, wherein the target cell is a cancer cell.
3. The molecular conjugate of embodiment 1 or 2, wherein the immune effector is a T cell modulator.
4. The molecular conjugate of any one of embodiments 1 to 3, wherein two or more antagonist molecules are conjugated to each immune effector molecule.
5. The molecular conjugate of embodiment 4, wherein the two or more antagonist molecules are a single type of antagonist molecules.
6. The molecular conjugate of embodiment 4, wherein the two more antagonist molecules are two or more different types of antagonist molecules.
7. The molecular conjugate of embodiment 1 or 2, wherein two or more immune effector molecules are conjugated to each antagonist molecule.
8. The molecular conjugate of embodiment 7, wherein the two or more immune effector molecules are a single type of immune effector molecule.
9. The molecular conjugate of embodiment 7, wherein the two or more immune effector molecules are two or more different types of effector molecules.
10. The molecular conjugate of embodiment 1 or 2, wherein the immune effector is one or more molecules selected from CD86, 41BBL, OX40, IL-15, Anti-Programmed Death-1 (PD1), anti-B7-H1, IL-12, Anti-CD40, CD40 ligand, IL-7, Anti-CD137 (anti-4-1BB), Anti-TGF-beta, Anti-IL-10 Receptor or Anti-IL-10, FMS-like Tyrosine Kinase 3 Ligand (Flt3L), Anti-Glucocorticoid-Induced TNF Receptor (GITR), chemokine (C-C motif) ligand 21 (CCL21), Anti-OX40, Anti-B7-H4, Anti-Lymphocyte Activation Gene-3 (LAG-3), CD258 (also referred to as LIGHT or TNFSF14), delta opioid receptor (DOR), or Anti-CTLA4 or an immune effector fragment of any of the foregoing.
11. The molecular conjugate of embodiment 2 or 3, wherein the cell surface receptor is selected from luteinizing hormone release hormone (LHRH) receptor, delta opioid receptor (DOR), melanocortin 1 receptor (MCR1), cell surface associated mucin 1 (MUC1), latent membrane protein 2 (LMP2), epidermal growth factor receptor variant III (EGFRvIII), human epidermal growth factor receptor 2 (HER-2/neu), prostate specific membrane antigen (PSMA), ganglioside antigen 2 (GD2), melanoma antigen recognized by T-cells 1 (MelanA/MART1), Ras mutant, glycoprotein 100, Proteinase3 (PR1), bcr-abl, tyrosinase, Androgen receptor, RhoC, transient receptor potential channel 2(TRP-2), prostate stem cell antigen (PSCA), leukocyte specific protein tyrosine kinase (LCK), high molecular weight melanoma-associated antigen (HMWMAA), A-kinase anchor protein 4 (AKAP-4), Angiopoietin-1 receptor (Tie 2), vascular endothelial growth factor receptor 2 (VEGFR2), fibroblast activation protein (FAP), platelet derived growth factor receptor b (PDGFR-b), parathyroid hormone related protein, leuteinizing hormone related protein, alpha(V)Beta(3)Integrin, six transmembrane antigen of the prostate (STEAP), mesothelin, endoglin, KCNK9, or guanylyl cyclase C (GC-C).
12. The molecular conjugate of any preceding embodiment, wherein the cancer cell is a breast cancer cell, prostate cancer cell, lung cancer cell, ovarian cancer cell, pancreatic cancer cell, or melanoma cell.
13. The molecular conjugate of any preceding embodiment, wherein the cell surface receptor is luteinizing hormone release hormone (LHRH) receptor, delta opioid receptor (DOR), or melanocortin 1 receptor (MCR1).
14. The molecular conjugate of embodiment 13, wherein the antagonist is a gonadotropin-releasing hormone antagonist (GnRH antagonist) or a delta opioid receptor (DOR) antagonist.
15. The molecular conjugate of embodiment 14, wherein the antagonist is Abarelix, Cetrorelix, Degarelix, Ganirelix, or DMT-Tic.
16. The molecular conjugate of any one of embodiments 1 to 9, wherein the antagonist is a luteinizing hormone releasing hormone (LHRH) antagonist, and the immune effector is CD86, 41BBL, OX40L, or a combination of two or three of the foregoing.
17. The molecular conjugate of any one of embodiments 1 to 9, wherein the antagonist is a luteinizing hormone releasing hormone (LHRH) antagonist, and the immune effector is CD40L, 41BB, CCL21, IL-12, or a combination of two or more of the foregoing.
18. The molecular conjugate of any one of embodiments 1 to 9, wherein the antagonist is a delta opioid receptor antagonist, and the immune effector is a T-cell modulator.
19. The molecular conjugate of embodiment 18, wherein the delta opioid receptor antagonist is Dmt-Tic.
20. The molecular conjugate of embodiment 18, wherein the T-cell modulator is anti-PD1, anti-PDL1, CD127L, OX40L, CD86, or a combination of two or more of the foregoing.
21. The molecular conjugate of any one of embodiments 1 to 20, further comprising an imaging agent.
22. A composition comprising a molecular conjugate according to any one of embodiments 1 to 21; and a pharmaceutically acceptable carrier.
23. The composition of embodiment 22, further comprising an additional bioactive agent.
24. The composition of embodiment 23, wherein the bioactive agent is an anti-cancer agent.
25. A method of treating a disease, the method comprising administering to a subject in need thereof a therapeutically effective amount of a molecular conjugate or composition according to any one of embodiments 1 to 24.

26. The method of embodiment 25, wherein the disease is cancer and the target cell is a cancer cell.

27. The method of embodiment 26, wherein the disease is breast cancer and the cancer cell is a breast cancer cell, or the disease is prostate cancer and the cancer cell is a prostate cancer cell, or the disease is lung cancer and the cancer cell is a lung cancer cell, or the disease is ovarian cancer and the cancer cell is an ovarian cancer cell, or the disease is pancreatic cancer and the cancer cell is a pancreatic cancer cell.

28. The method of embodiment 26, wherein the antagonist is a luteinizing hormone releasing hormone (LHRH) antagonist; wherein the immune effector is CD86, 41BBL, OX40L, or a combination of two or three of the foregoing; and wherein the cancer is breast cancer and the target cell is a breast cancer cell.

29. The method of embodiment 26, wherein the antagonist is a luteinizing hormone releasing hormone (LHRH) antagonist; wherein the immune effector is CD40L, 41BB, CCL21, IL-12, or a combination of two or more of the foregoing; and wherein the cancer is ovarian cancer and the target cell is an ovarian cancer cell.

30. The method of embodiment 26, wherein the antagonist is a delta opioid receptor antagonist; wherein the immune effector is a T-cell modulator; and wherein the cancer is non-small cell lung cancer (NSCLC) and the target cell is an NSCLC cell.

31. The method of embodiment 30, wherein the delta opioid receptor antagonist is DMT-Tic.

32. The method of any one of embodiments 25 to 31, wherein the molecular conjugate further comprises an imaging agent.

33. The method of any one of embodiments 25 to 32, further comprising administering a bioactive agent to the subject simultaneously or consecutively with the molecular conjugate.

34. The method of embodiment 33, wherein the bioactive agent is an anti-cancer agent.

35. The method of embodiment 33 or 34, wherein the bioactive agent is administered within the same formulation as the molecular conjugate.

36. The method of embodiment 33 or 34, wherein the bioactive agent is administered within a formulation that is separate from the molecular conjugate.

37. A method for delivering a molecular conjugate to a cell, the method comprising administering to the cell in vitro or in vivo a molecular conjugate according to any one of embodiments 1 to 24.

38. The method of embodiment 37, wherein the cell is a diseased cell.

39. The method of embodiment 37 or 38, wherein the cell is a cancer cell.

REFERENCES

1. Javadpour M M, Juban M M, Lo W C, Bishop S M, Alberty J B, Cowell S M, Becker C L, McLaughlin M L. De novo antimicrobial peptides with low mammalian cell toxicity. Journal of medicinal chemistry. 1996; 39(16): 3107-13.
2. Reissmann T, Schally A V, Bouchard P, Riethmüller H, Engel J. The LHRH antagonist cetrorelix: a review. Human reproduction update. 2000; 6(4):322-31. Epub Sep. 6, 2000.
3. Korman A J, Peggs K S, Allison J P. Checkpoint blockade in cancer immunotherapy. Advances in immunology. 2006; 90:297-339. Epub May 30, 2006.
4. Brahmer J R, Pardoll D M. Immune checkpoint inhibitors: making immunotherapy a reality for the treatment of lung cancer. Cancer immunology research. 2013; 1(2):85-91. Epub Apr. 4, 2014.
5. Kyi C, Postow M A. Checkpoint blocking antibodies in cancer immunotherapy. FEBS letters. 2014; 588(2):368-76. Epub Oct. 29, 2013.
6. Nirschl C J, Drake C G. Molecular pathways: coexpression of immune checkpoint molecules: signaling pathways and implications for cancer immunotherapy. Clinical cancer research: an official journal of the American Association for Cancer Research. 2013; 19(18):4917-24. Epub Jul. 23, 2013.
7. Li G, Wu X, Zhang F, Li X, Sun B, Yu Y, Yin A, Deng L, Yin J, Wang X. Triple expression of B7-1, B7-2 and 4-1BBL enhanced antitumor immune response against mouse H22 hepatocellular carcinoma. Journal of cancer research and clinical oncology. 2011; 137(4):695-703. Epub Jun. 22, 2010.
8. Creelan B C, Antonia S, Bepler G, Garrett T J, Simon G R, Soliman H H. Indoleamine 2,3-dioxygenase activity and clinical outcome following induction chemotherapy and concurrent chemoradiation in Stage III non-small cell lung cancer. Oncoimmunology. 2013; 2(3):e23428. Epub Jun. 27, 2013.
9. Soliman H, Rawal B, Fulp J, Lee J H, Lopez A, Bui M M, Khalil F, Antonia S, Yfantis H G, Lee D H, Dorsey T H, Ambs S. Analysis of indoleamine 2-3 dioxygenase (IDO1) expression in breast cancer tissue by immunohistochemistry. Cancer immunology, immunotherapy: CII. 2013; 62(5):829-37. Epub Jan. 25, 2013.
10. Chiappori A A, Soliman H, Janssen W E, Antonia S J, Gabrilovich D I. INGN-225: a dendritic cell-based p53 vaccine (Ad.p53-DC) in small cell lung cancer: observed association between immune response and enhanced chemotherapy effect. Expert opinion on biological therapy. 2010; 10(6):983-91. Epub Apr. 28, 2010.
11. Fishman M, Hunter T, Soliman H, Thompson P, Dunn M, Smilee R, Farmelo M, Noyes D, Mahany J, Lee J, Cantor A, Messina J, Seigne J, Pow-Sang J, Janssen W, Antonia S. Phase II trial of B7-2 (CD-86) transduced, cultured autologous tumor cell vaccine plus subcutaneous interleukin-2 for treatment of stage IV renal cell carcinoma. J Immunother. 2008; January; 31(1):72-80.
12. Jackson E, Soliman H. Realizing the promise of breast cancer vaccines. Vaccine: Development and Therapy. 2012; August (2):35-41.
13. Soliman H. Developing an effective breast cancer vaccine. Cancer control: journal of the Moffitt Cancer Center. 2010; 17(3):183-90. Epub Jul. 29, 2010.
14. Soliman H. Immunotherapy strategies in the treatment of breast cancer. Cancer control: journal of the Moffitt Cancer Center. 2013; 20(1):17-21. Epub Jan. 11, 2013.
15. Soliman H, Khalil F, Antonia S. PD-L1 Expression Is Increased in a Subset of Basal Type Breast Cancer Cells. PLOS ONE. 2014; 9(2):e88557.
16. Rohrbach F, Gerstmayer B, Biburger M, Wels W. Construction and characterization of bispecific costimulatory molecules containing a minimized CD86 (B7-2) domain and single-chain antibody fragments for tumor targeting. Clinical cancer research: an official journal of the American Association for Cancer Research. 2000; 6(11):4314-22. Epub Dec. 6, 2000.
17. Won E Y, Cha K, Byun J S, Kim D U, Shin S, Ahn B, Kim Y H, Rice A J, Walz T, Kwon B S, Cho H S. The structure of the trimer of human 4-1BB ligand is unique among members of the tumor necrosis factor superfamily. The Journal of biological chemistry. 2010; 285(12):9202-10. Epub Dec. 25, 2009.
18. Compaan D M, Hymowitz S G. The crystal structure of the costimulatory OX40-OX40L complex. Structure. 2006; 14(8):1321-30. Epub Aug. 15, 2006.
19. Wynn P C, Suarez-Quian C A, Childs G V, Catt K J. Pituitary binding and internalization of radioiodinated gonadotropin-releasing hormone agonist and antagonist ligands in vitro and in vivo. Endocrinology. 1986; 119(4):1852-63.
20. Muller A, Busker E, Engel J, Kutscher B, Bernd M, Schally A V. Structural investigation of Cetrorelix, a new potent and long-acting LH-RH antagonist. International journal of peptide and protein research. 1994; 43(3):264-70.
21. Buchholz S, Seitz S, Schally A V, Engel J B, Rick F G, Szalontay L, Hohla F, Krishan A, Papadia A, Gaiser T, Brockhoff G, Ortmann O, Diedrich K, Koster F. Triple-negative breast cancers express receptors for luteinizing hormone-releasing hormone (LHRH) and respond to LHRH antagonist cetrorelix with growth inhibition. International journal of oncology. 2009; 35(4):789-96. Epub Sep. 3, 2009.
22. Jiang G C, Stalewski J, Galyean R, Dykert J, Schteingart C, Broqua P, Aebi A, Aubert M L, Semple G, Robson P, Akinsanya K, Haigh R, Riviere P, Trojnar J, Junien J L, Rivier J E. GnRH antagonists: A new generation of long acting analogues incorporating p-ureido-phenylalanines at positions 5 and 6. Journal of medicinal chemistry. 2001; 44(3):453-67.
23. Gebhard A W, Jain P, Nair R R, Emmons M F, Argilagos R F, Koomen J M, McLaughlin M L, Hazlehurst L A. MTI-101 (cyclized HYD1) binds a CD44 containing complex and induces necrotic cell death in multiple myeloma. Molecular cancer therapeutics. 2013; 12(11):2446-58. Epub Sep. 21, 2013
24. Shapiro G, Buchler D, Dalvit C, Frey P, Fernandez M C, Gomez-Lor B, Pombo-Villar E, Stauss U, Swoboda R, Waridel C. Combined Fmoc-Alloc strategy for a general SPPS of phosphoserine peptides; preparation of phosphorylation-dependent tau antisera. Bioorganic & medicinal chemistry. 1997; 5(1):147-56. Epub Jan. 1, 1997.
25. Tafreshi N K, Huang X, Moberg V E, Barkey N M, Sondak V K, Tian H, Morse D L, Vagner J. Synthesis and characterization of a melanoma-targeted fluorescence imaging probe by conjugation of a melanocortin 1 receptor (MC1R) specific ligand. Bioconjugate chemistry. 2012; 23(12):2451-9. Epub Nov. 3, 2012.
26. Tafreshi N K, Enkemann S A, Bui M M, Lloyd M C, Abrahams D, Huynh A S, Kim J, Grobmyer S R, Carter W B, Vagner J, Gillies R J, Morse D L. A mammaglobin-A targeting agent for noninvasive detection of breast cancer metastasis in lymph nodes. Cancer research. 2011; 71(3):1050-9. Epub Dec. 21, 2010.
27. Tafreshi N K, Bui M M, Bishop K, Lloyd M C, Enkemann S A, Lopez A S, Abrahams D, Carter B W, Vagner J, Grobmyer S R, Gillies R J, Morse D L. Noninvasive detection of breast cancer lymph node metastasis using carbonic anhydrases IX and XII targeted imaging probes. Clinical cancer research: an official journal of the American Association for Cancer Research. 2012; 18(1):207-19. Epub Oct. 22, 2011.
28. Huynh A S, Chung W J, Cho H I, Moberg V E, Celis E, Morse D L, Vagner J. Novel toll-like receptor 2 ligands for targeted pancreatic cancer imaging and immunotherapy. Journal of medicinal chemistry. 2012; 55(22):9751-62. Epub Oct. 27, 2012.
29. Tafreshi N K, Silva A, Estrella V C, McCardle T W, Chen T, Jeune-Smith Y, Lloyd M C, Enkemann S A, Smalley K S, Sondak V K, Vagner J, Morse D L. In vivo and in silico pharmacokinetics and biodistribution of a melanocortin receptor 1 targeted agent in preclinical models of melanoma. Molecular pharmaceutics. 2013; 10(8):3175-85. Epub Jun. 15, 2013.
30. Morse D L, Raghunand N, Sadarangani P, Murthi S, Job C, Day S, Howison C, Gillies R J. Response of choline metabolites to docetaxel therapy is quantified in vivo by localized (31)P MRS of human breast cancer xenografts and in vitro by high-resolution (31)P NMR spectroscopy of cell extracts. Magnetic resonance in medicine: official journal of the Society of Magnetic Resonance in Medicine/Society of Magnetic Resonance in Medicine. 2007; 58(2):270-80. Epub Jul. 27, 2007.
31. Morse D L, Carroll D, Day S, Gray H, Sadarangani P, Murthi S, Job C, Baggett B, Raghunand N, Gillies R J. Characterization of breast cancers and therapy response by MRS and quantitative gene expression profiling in the choline pathway. NMR in biomedicine. 2009; 22(1):114-27. Epub Nov. 20, 2008.
32. Hanahan D, Weinberg R A. Hallmarks of cancer: the next generation. Cell. 2011; 144(5):646-74.
33. Wolchok J D, Kluger H, Callahan M K, Postow M A, Rizvi N A, Lesokhin A M, Segal N H, Ariyan C E, Gordon R A, Reed K, Burke M M, Caldwell A, Kronenberg S A, Agunwamba B U, Zhang X, Lowy I, Inzunza H D, Feely W, Horak C E, Hong Q, Korman A J, Wigginton J M, Gupta A, Sznol M. Nivolumab plus ipilimumab in advanced melanoma. The New England journal of medicine. 2013; 369(2):122-33.
34. Josan J S, Morse D L, Xu L, Trissal M, Baggett B, Davis P, Vagner J, Gillies R J, Hruby V J. Solid-phase synthetic strategy and bioevaluation of a labeled delta-opioid receptor ligand Dmt-Tic-Lys for in vivo imaging. Organic letters. 2009; 11(12):2479-82. Epub May 19, 2009.
35. Peng J, Sarkar S, Chang S L. Opioid receptor expression in human brain and peripheral tissues using absolute quantitative real-time RT-PCR. Drug and alcohol dependence. 2012; 124(3):223-8. Epub Feb. 24, 2012.
36. Schreiber G, Campa M J, Prabhakar S, O'Briant K, Bepler G, Patz E F, Jr. Molecular characterization of the human delta opioid receptor in lung cancer. Anticancer research. 1998; 18(3A):1787-92. Epub Jul. 23, 1998.
37. Ryu E K, Wu Z, Chen K, Lazarus L H, Marczak E D, Sasaki Y, Ambo A, Salvadori S, Ren C, Zhao H, Balboni G, Chen X. Synthesis of a potent and selective (18)F-labeled delta-opioid receptor antagonist derived from the Dmt-Tic pharmacophore for positron emission tomography imaging. Journal of medicinal chemistry. 2008; 51(6):1817-23. Epub Mar. 4, 2008.
38. Ascierto P A, Simeone E, Sznol M, Fu Y X, Melero I. Clinical experiences with anti-CD137 and anti-PD1 therapeutic antibodies. Seminars in oncology. 2010; 37(5):508-16.
39. Chacon J A, Wu R C, Sukhumalchandra P, Molldrem J J, Sarnaik A, Pilon-Thomas S, Weber J, Hwu P, Radvanyi L. Co-stimulation through 4-1BB/CD137 improves the expansion and function of CD8(+) melanoma tumor-infiltrating lymphocytes for adoptive T-cell therapy. PLoS One. 2013; 8(4):e60031.
40. Ye Q, Song D G, Poussin M, Yamamoto T, Best A, Li C, Coukos G, Powell D J, Jr. CD137 accurately identifies and enriches for naturally occurring tumor-reactive T cells in tumor. Clinical cancer research: an official journal of the American Association for Cancer Research. 2014; 20(1): 44-55.
41. Curti B D, Kovacsovics-Bankowski M, Morris N, Walker E, Chisholm L, Floyd K, Walker J, Gonzalez I, Meeuwsen T, Fox B A, Moudgil T, Miller W, Haley D, Coffey T, Fisher B, Delanty-Miller L, Rymarchyk N, Kelly T, Crocenzi T, Bernstein E, Sanborn R, Urba W J, Weinberg A D. OX40 is a potent immune-stimulating target in late-stage cancer patients. Cancer research. 2013; 73(24):7189-98.
42. Beatty G L, Chiorean E G, Fishman M P, Saboury B, Teitelbaum U R, Sun W, Huhn R D, Song W, Li D, Sharp L L, Torigian D A, O'Dwyer P J, Vonderheide R H. CD40 agonists alter tumor stroma and show efficacy against pancreatic carcinoma in mice and humans. Science. 2011; 331(6024):1612-6.
43. Reissmann T, Schally A V, Bouchard P, Riethmiiller H, Engel J. The LHRH antagonist cetrorelix: a review. Human reproduction update. 2000; 6(4):322-31. Epub Sep. 6, 2000.
44. el-Shami K, Tirosh B, Bar-Haim E, Carmon L, Vadai E, Fridkin M, Feldman M, Eisenbach L. MHC class I-restricted epitope spreading in the context of tumor rejection following vaccination with a single immunodominant CTL epitope. European journal of immunology. 1999; 29(10):3295-301.
45. Markiewicz M A, Fallarino F, Ashikari A, Gajewski T F. Epitope spreading upon P815 tumor rejection triggered by vaccination with the single class I MHC-restricted peptide P1A. International immunology. 2001; 13(5):625-32.
46. Vanderlugt C L, Miller S D. Epitope spreading in immune-mediated diseases: implications for immunotherapy. Nature reviews Immunology. 2002; 2(2):85-95.
47. Pilon S A, Kelly C, Wei W Z. Broadening of epitope recognition during immune rejection of ErbB-2-positive tumor prevents growth of ErbB-2-negative tumor. Journal of immunology. 2003; 170(3):1202-8.
48. Hopewell E L, Zhao W, Fulp W J, Bronk C C, Lopez A S, Massengill M, Antonia S, Celis E, Haura E B, Enkemann S A, Chen D T, Beg A A. Lung tumor NF-kappaB signaling promotes T cell-mediated immune surveillance. The Journal of clinical investigation. 2013; 123(6):2509-22. Epub May 3, 2015.
49. Beg A A, Khan T, Antonia S J. A new role for NFkappaB in immunosurveillance and its implications for cancer immunotherapy. Oncoimmunology. 2013; 2(10):e25963. Epub Jan. 10, 2014.
50. Simon G R, Schell M J, Begum M, Kim J, Chiappori A, Haura E, Antonia S, Bepler G. Preliminary indication of survival benefit from ERCC1 and RRM1-tailored chemotherapy in patients with advanced nonsmall cell lung cancer: evidence from an individual patient analysis. Cancer. 2012; 118(9):2525-31. Epub Oct. 27, 2011.
51. Chames P, Baty D. Bispecific antibodies for cancer therapy: the light at the end of the tunnel? mAbs. 2009; 1(6):539-47.
52. Baeuerle P A, Reinhardt C. Bispecific T-cell engaging antibodies for cancer therapy. Cancer research. 2009; 69(12):4941-4.
53. Brischwein K, Parr L, Pflanz S, Volkland J, Lumsden J, Klinger M, Locher M, Hammond S A, Kiener P, Kufer P, Schlereth B, Baeuerle P A. Strictly target cell-dependent activation of T cells by bispecific single-chain antibody constructs of the BiTE class. J Immunother. 2007; 30(8): 798-807.

We claim:
1. A molecular conjugate comprising:
   a) a luteinizing hormone releasing hormone (LHRH) peptide antagonist; and
   b) an immune effector molecule conjugated to the antagonist, wherein the immune effector molecule is selected from the group consisting of CD86, 41BBL, OX40L, or a combination of two or three thereof, or wherein the immune effector molecule is selected from the group consisting of CD40L, 41BB, CCL21, IL-12, or a combination of two or more thereof.
2. The molecular conjugate of claim 1, wherein two or more antagonist molecules are conjugated to the immune effector molecule.
3. The molecular conjugate of claim 1, wherein two or more immune effector molecules are conjugated to the antagonist molecule.
4. The molecular conjugate of claim 3, wherein the two or more immune effector molecules are a single type of immune effector molecule.
5. The molecular conjugate of claim 3, wherein the two or more immune effector molecules are two or more different types of effector molecules.
6. The molecular conjugate of claim 1, further comprising an imaging agent.
7. The molecular conjugate of claim 1, further comprising:
   a pharmaceutically acceptable carrier.
8. A method of treating a cancer which expresses LHRH receptor, the method comprising administering to a subject in need thereof a therapeutically effective amount of a molecular conjugate according to claim 1.
9. A method for delivering a molecular conjugate to a cancer cell expressing LHRH receptor, the method comprising administering to the cell in vitro or in vivo a molecular conjugate of claim 1.

* * * * *